United States Patent
Fan et al.

[11] Patent Number: 6,124,483
[45] Date of Patent: *Sep. 26, 2000

[54] PROCESS FOR PREPARING UNSATURATED ESTERS CONTAINING CYCLIC EPOXY GROUP

[75] Inventors: Mingxin Fan, West Chester; Gary W. Ceska, Exton; James Horgan, West Chester, all of Pa.

[73] Assignee: Sartomer Technology Company, Exton, Pa.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/773,524

[22] Filed: Dec. 23, 1996

[51] Int. Cl.⁷ .................................................. C07D 301/12
[52] U.S. Cl. ............................................ 549/531; 549/530
[58] Field of Search ............................................... 549/531

[56] References Cited

U.S. PATENT DOCUMENTS

| | | | |
|---|---|---|---|
| 2,833,787 | 5/1958 | Carlson et al. | 549/531 |
| 3,459,775 | 8/1969 | Rick et al. | 549/554 |
| 5,036,154 | 7/1991 | Au | 549/531 |
| 5,274,140 | 12/1993 | Venturello et al. | 549/531 |
| 5,283,360 | 2/1994 | Caubere et al. | 560/220 |
| 5,481,012 | 1/1996 | Caubere et al. | 549/531 |

FOREIGN PATENT DOCUMENTS 5-247402  9/1993  Japan .

OTHER PUBLICATIONS

CRC Handbook of Chemistry and Physics, 64th edition, 1984, edited by Robert C. Weast, pp. B–64, B–143 and B–153.

*Primary Examiner*—Bernard Dentz
*Attorney, Agent, or Firm*—Michael Fein; Cozen & O'Connor

[57] ABSTRACT

Process of making compounds of the formula

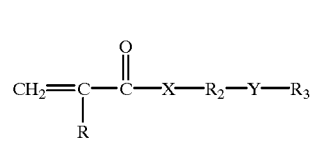

(I)

wherein $R_1 = (C_1–C_6)$ alkyl;
X = O, S, NH;
$R_2$ = divalent saturated organic group;
Y = O, S, NH, ester;
$R_3$ = cyclic moiety containing oxirane group;

comprising reacting a compound of the formula

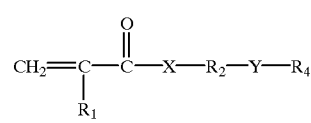

(II)

wherein $R_4$ is a cyclic moiety containing C=C group with hydrogen peroxide in the presence of (a) tungstic acid, (b) phosphoric acid or its metal salts, and (c) at least one phase transfer catalyst;

polymers of compounds of formula I; and compounds of formula I except for compounds wherein $R_4$ is a dicyclopentenyl epoxide, Y is O, $R_2$ is —CH₂CH₂—, X is O, and $R_1$ is H or methyl.

14 Claims, No Drawings

PROCESS FOR PREPARING UNSATURATED ESTERS CONTAINING CYCLIC EPOXY GROUP

BACKGROUND OF THE INVENTION

1. Field of the Invention

This invention relates to epoxidation of unsaturated (meth)acrylate esters.

2. Description of the Prior Art (Meth)acrylate monomers which have epoxide functional groups are widely used in industry as chemical intermediates for synthetic materials. Traditionally, these monomers are being produced from epichlorohydrin via coupling with corresponding salts. Epoxidation of unsaturated organic substrates without (meth)acrylate functional groups is much easier due to the lack of (meth)acrylate functional group polymerization initiated by peroxide or radicals generated in situ. U.S. Pat. Nos. 2,833,787 and 2,833,788 describe the epoxidation of nonconjugated ethylenic compounds by hydrogen peroxide and water soluble sodium pertungstate at a PH of between 3 and 7. Similarly, unsaturated acids were epoxidized by hydrogen peroxide and sodium tungstate (J. Org. Chem., vol. 24, 54).

Olefin epoxidation using hydrogen peroxide and a water soluble alkali metal tungstate in the presence of a phase transfer agent was reported (J. Org. Chem., vol. 48, 3831 and J. Org. Chem., vol. 50, 2688). Similarly, water soluble molybdophosphoric and tungstophosphoric acid (hetero polyacids) were used in the catalytic epoxidation of olefins using hydrogen peroxide (J. Org. Chem., vol. 52, 1868 and vol. 53,3587).

The epoxidation of unsaturated (meth)acrylate esters using peracetic acid was described in U.S. Pat. No. 3,459,775 in very low yield. U.S. Pat. No. 5,283,360 describes the selective epoxidation of unsaturated (meth)acrylates using hydrogen peroxide in the presence of water soluble alkali metal molybdates and tungstates as well as heteropolyacid for cyclic substrates and phase transfer agent. According to U.S. Pat. No. 5,283,360, conversion was less than 100% and residual allylic compound.

U.S. Pat. Nos. 5,783,360 and 5,510,516 to Caubere, et al, shows epoxidation of unsaturated (meth)acrylate esters with hydrogen peroxide using a catalyst system which comprises alkali metal salts of tungstic or molybdic acids and a heteropolyacid. Caubere et al do not show (meth)acrylates which have been alkoxylated, nor do they show phosphoric acid.

GB application 2 055821A by Venturello, et al, shows epoxidation of olefins with hydrogen peroxide using a catalyst system consisting of W, Mo, or V, and at least one derivative of P or As. This application does not show epoxidation of (meth)acrylates or alkoxylated compounds.

One of the problems of the prior art processes is low catalyst lifetime and low catalytic conversion. Low conversion results in contamination with the starting material which causes crosslinking during free radical polymerization. Prior art catalytic systems include water soluble alkali metal salts of molybdates and tungstates as well as their heteropolyacids. In the presence of phase transfer agent the conversion is low and residual unsaturated (meth)acrylate remains in the initial product mixture, resulting in low stability and crosslinking in some applications. Prior art in the field requires water soluble alkali metal salts of molybdate and tungstates and their heteropolyacids.

SUMMARY OF THE INVENTION

It is therefore an object of the present invention to provide an improved method of selectively epoxidizing compounds having acrylate or methacrylate groups.

It is also an object of the invention to provide a new class of (meth)acrylates containing epoxide functionalities.

A further object of the invention is to provide a method of epoxidizing (meth)acrylates which has improved catalyst life and higher than previously achieved yields.

These objects, and others which will become apparent from the following disclosure are achieved by the present invention which comprises in one aspect a process for selectively epoxidizing (meth)acrylate monomers using hydrogen peroxide as oxidizing agent and a catalyst system comprising water insoluble tungstic acid in combination with phosphoric acid in the presence of phase transfer agent.

Another aspect of the invention is a process for epoxidizing (meth)acrylate monomers which results in complete conversion comprising using insoluble tungstic acid and phosphoric acid with or without any acidity adjustment.

DETAILED DESCRIPTION OF INVENTION AND PREFERRED EMBODIMENTS

The current invention will result in complete conversion of unsaturated (meth)acrylate esters to (meth)acrylate epoxides using insoluble tungstic acid and phosphoric acid with or without any acidity adjustment.

The catalyst composition used in the process of the invention is highly effective and selective, which is very advantageous in the epoxidation of unsaturated (meth) acrylate monomers.

The new method involves low level of catalyst composition. Furthermore, no organic acid and/or peracid is used which results in simple product workup and process.

The present invention uses hydrogen peroxide in the presence of (a) tungstic acid or its metal salts, (b) phosphoric acid or its metal salts, (c) at least one phase transfer catalyst. The epoxidation of unsaturated (meth)acrylates with hydrogen peroxide in the presence of tungsten catalyst, phosphoric acid or its salt, and phase transfer catalyst can be performed at any temperature which is sufficient to react, however, particularly suitable temperatures are between 0° C. and 100° C., preferably from 25° C. to 70° C. The reaction takes place faster at higher temperature and requires shorter time to complete, the reaction is typically exothermic and slow addition of hydrogen peroxide is preferred to control the exotherm. At higher temperature, hydrogen peroxide undergoes decomposition. The reaction can be performed at pressures from subatmospheric to superatmospheric pressures; however, the reaction is preferably carried out at atmospheric pressure.

The epoxidation can be performed with or without solvent, solvent can be used to reduce the viscosity, if solvent is needed, a water immissible organic solvent such as chlorinated hydrocarbons, ethers, glycol ethers, hydrocarbons, combinations thereof. Particular suitable organic solvents are toluene, chlorobenzene, chloroform, methylene chloride heptane, and the like.

Hydrogen peroxide solution is used as oxidant in the concentration of 5 to 70%. The amount of hydrogen peroxide can vary depending on the desired degree of epoxidation, typically from 0.1 to 1.5 equivalent C=C in the starting material.

The phase transfer catalyst can be used from 0.001 to 1.5, preferably 0.05 to 0.1, equivalents per equivalent of carbon carbon double bond. Suitable phase transfer catalysts includes quaternary ammonium salts, quaternary phosphoniumsalts, polyethers. The method of the invention comprises a process

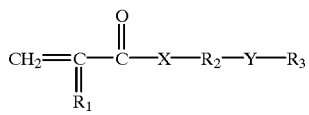

wherein
$R_1 = (C_1-C_6)$ alkyl;
X = O, S, NH;
$R_2$ = divalent organic group;
Y = O, S, NH, ester;
$R_3$ = cyclic moiety containing oxirane group;
comprising reacting a compound of the formula

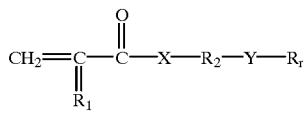

wherein $R_4$ is a cyclic moiety containing C=C group with hydrogen peroxide in the presence of (a) tungstic acid or its metal salts, (b) phosphoric acid or its metal salts, and (c) at least one phase transfer catalyst.

The resultant compounds are novel, except when $R_4$ is a dicyclopentenyl epoxide, Y is O, $R_2$ is —$CH_2CH_2$—, X is O, and $R_1$ is H or methyl.

Preferred compounds are those wherein $R_1$ is H or methyl, i.e., acrylates or methacrylates, and those wherein X is O and $R_2$ is $(C_1-C_{10})$ alkylene.

Especially preferred compounds are those wherein $R_4$ is unsubstituted or substituted cyclohexenyl. While any substituent can be used, preferred are alkyl or ester, for example, methyl or

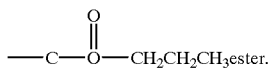

Phosphoric acid or its various salts can be used from 0.001 to 0.5 equivalents per equivalent of carbon carbon double bond. Sodium or potassium salts of monobasic, dibasic, or tribasic salts of phosphoric acid can also be used. The final pH can be adjusted by other acids or bases to 0–5.

Tungstic acid or its metal salts can be used as the metal catalysts, the metal salts are water soluble and the acid is not. The typical catalyst is used from 0.005 to 1% and the preferred catalyst is tungstic acid which is not water soluble.

The epoxidized unsaturated (meth)acrylates can be used in a variety of applications, such as coatings, epoxy/amine cure, cationic cure, and chemical intermediates for polymers and oligomers.

The compounds of formula I can be used to make novel polymers, both homo- and copolymers. Especially useful polymers are copolymers of a compound of formula I and one or more acrylates, methacrylates, epoxy compounds. Also preferred are copolymers (A) a compound of formula I; (B) an epoxy compound not containing an acrylate or methacrylate group, and (C) an acrylate or methacrylate compound not containing an epoxy group.

The polymers can be prepared by exposing the monomer or monomer mixture to radiation according to methods known in the art.

In some embodiments, the monomers are first reacted via free radical polymerization and then cured via the epoxy groups. In other embodiments the epoxy groups can be polymerized using cationic initiator.

A preferred embodiment is when both free radical initiator and cationic initiator are present and the mixture is exposed to radiation to form a cured polymer.

The cured polymers can be used for coatings, sealants, adhesives, inks, and the like.

EXAMPLES

The following non-limiting examples are presented to illustrate a few embodiments of the invention. All parts and percentages are by weight unless otherwise indicated.

Example 1

Epoxidation of Ethylene Glycol Dicyclopentenyl Ether Methacrylate

In a four-necked flask tungstic acid (1.50 g), sodium hydroxide (25%, 0.75 ml), and phosphoric acid (85%, 0.50 ml) were added, followed by addition of ethylene glycol dicyclopentenyl ether methacrylate (131.0 g 0.5 mole), toluene (131.0 g), and trioctyl methyl ammonium chloride (1.50 g). The resultant mixture was stirred to form a yellow mixture and heated to 60° C., after which hydrogen peroxide (30%, 100.0 ml) was added slowly over 50 min. The reaction mixture was stirred at 60° C. for 2½ hours.

GC analysis showed no starting material left and 100% conversion to epoxide was obtained.

Example 2

Epoxidation of Dicyclopentadienyl Methacrylate

Following the same procedure, dicyclopentadienyl methacrylate was epoxidized with 100% conversion.

Example 3

Epoxidation of Dicyclopentenyl Acrylate

Following the sample procedure, dicyclopentenyl acrylate was epoxidized with 100% conversion.

Example 4

Epoxidation of Ethylene Glycol Dicyclopentenyl Ether Methacrylate

Example 1 was repeated without sodium hydroxide. The material was epoxidized with 100% conversion.

Example 5

Synthesis of Unsaturated Methacrylate Ester

In a four-necked flask, tetrahydrophthalic anhydride (152.1 g), hydroxyethyl methacrylate (130.0 g), and methoxyphenol (0.30 g) were added and stirred, and air sparge was applied while stirring. The mixture was heated to 100° C. for six hours. IR showed no anhydride starting material left.

To the above product, 1-propanol (84.0 g), methoxyphenol (2.0 g), toluene (75.0 g), heptane (75.0 g), methanesulfonic acid (70%, 10.0 g) were added, air sparge applied, the mixture was stirred and refluxed. Water was removed azeotropically during the reaction and the esterification reaction completed in 5.0 hours. The final mixture was neutralized and washed with 25% NaOH and solvent was stripped at 25 mmHg at 95° C. 273.0 g clear light yellow unsaturated methacrylate was obtained.

Example 6

Epoxidation of Unsaturated Methacrylate Ester from Example 5

100.0 g unsaturated methacrylate ester from Example 5, 100.0 g toluene, 0.80 g trioctylmethyl ammonium chloride, 0.80 g tungstic acid, 0.40 g sodium hydroxide (25%), and 0.40 g phosphoric acid (85%) were added to a reactor, and the mixture was stirred and heated to 60° C. Then 100 ml $H_2O_2$ (30%) was slowly added within 30 min. and the temperature was controlled at 60° C. The reaction mixture was kept at 60° C. for additional 3½ hours. The unsaturated methacrylate was completely epoxidized based on GC analysis.

While the invention has been described in sufficient detail for those skilled in the art to make and use it, various modifications, alternatives, and improvements should become readily apparent without departing from the spirit and scope of the invention as set forth in the following claims.

What is claimed is:

1. Process of making compounds of the formula

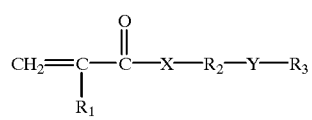

(I)

wherein
$R_1 = (C_1-C_6)$ alkyl;
X = O, S, NH;
$R_2$ = divalent saturated organic group;
Y = O, S, NH, ester;
$R_3$ = cyclic moiety containing oxirane group;
comprising reacting a compound of the formula

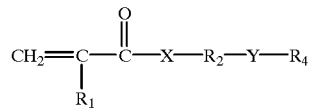

(II)

wherein $R_4$ is a cyclic moiety containing C=C group with hydrogen peroxide in the presence of (a) tungstic acid, (b) phosphoric acid or its metal salts, and (c) at least one phase transfer catalyst.

2. Process according to claim 1 wherein said hydrogen peroxide is introduced in an amount of about 0.1 to 1.5 equivalent per equivalent of C=C group in $R_3$.

3. Process according to claim 1 wherein the reacting is conducted at a temperature of about 0° C. to 100° C.

4. Process according to claim 1 wherein the reacting is conducted at a temperature of about 25° C. to 70° C.

5. Process according to claim 1 wherein the phase transfer catalyst is present in an amount of about 0.001 to 1.5 equivalents per equivalent of C=C group in $R_4$.

6. Process according to claim 1 wherein the phase transfer catalyst is present in an amount of about 0.05 to 0.1 equivalents per equivalent of C=C group in $R_4$.

7. Process according to claim 1 wherein the phase transfer catalyst is selected from the group consisting of quaternary ammonium salts, quaternary phosphonium salts, and polyethers.

8. Process according to claim 1 wherein the reaction is conducted in the presence of a water immiscible organic solvent.

9. Process according to claim 1 wherein the reaction is conducted in the presence of a water immiscible organic solvent selected from the group consisting of chlorinated hydrocarbons, ethers, glycol ethers, aliphatic and aromatic hydrocarbons, and combinations thereof.

10. Process according to claim 9 wherein the solvent is selected from the group consisting of toluene, chlorobenzene, chloroform, heptane, and methylene chloride.

11. Process according to claim 1 wherein the phosphoric acid or phosphoric acid salt comprises about 0.001 to 0.5 equivalents per equivalent of C=C group in $R_4$.

12. Process according to claim 1 wherein the phosphoric acid or salt thereof is a sodium or potassium salt of monobasic, dibasic, or tribasic phosphoric acid.

13. Process according to claim 1 wherein the pH of the reaction is adjusted by acids or bases to about 0–5.

14. Process according to claim 1 wherein the tungstic acid is present in and amount of about 0.005 to 1% based on weight of compound of formula II.

* * * * *